US008518915B2

(12) United States Patent
Skulachev et al.

(10) Patent No.: US 8,518,915 B2
(45) Date of Patent: Aug. 27, 2013

(54) USE OF MITOCHONDRIALLY-ADDRESSED COMPOUNDS FOR PREVENTING AND TREATING CARDIOVASCULAR DISEASES

(75) Inventors: Maxim Vladimirovich Skulachev, Moscow (RU); Vladimir Petrovich Skulachev, Moscow (RU)

(73) Assignee: Mitotech SA, Luxembourg (LU)

( * ) Notice: Subject to any disclaimer, the term of this patent is extended or adjusted under 35 U.S.C. 154(b) by 291 days.

(21) Appl. No.: 12/667,061

(22) PCT Filed: Jun. 29, 2007

(86) PCT No.: PCT/RU2007/000355
§ 371 (c)(1),
(2), (4) Date: Nov. 17, 2010

(87) PCT Pub. No.: WO2009/005386
PCT Pub. Date: Jan. 8, 2009

(65) Prior Publication Data
US 2011/0053895 A1    Mar. 3, 2011

(51) Int. Cl.
*A61K 31/66* (2006.01)
*A61K 31/352* (2006.01)
*A61P 9/00* (2006.01)
*A61P 39/06* (2006.01)

(52) U.S. Cl.
USPC ............ 514/125; 514/129; 514/453; 514/459; 549/227; 568/9; 568/13; 568/17

(58) Field of Classification Search
USPC ............... 514/125, 129, 453, 459; 549/227; 568/9, 13, 17
See application file for complete search history.

(56) References Cited

U.S. PATENT DOCUMENTS

| | | | |
|---|---|---|---|
| 5,538,974 A | 7/1996 | Ogawa et al. | |
| 6,331,532 B1 | 12/2001 | Murphy et al. | |
| 7,109,189 B2 | 9/2006 | Murphy et al. | |
| 2005/0065099 A1 | 3/2005 | Walkinshaw et al. | |
| 2007/0259908 A1 | 11/2007 | Fujii et al. | |
| 2007/0270381 A1 | 11/2007 | Murphy et al. | |
| 2008/0275005 A1 | 11/2008 | Murphy et al. | |
| 2010/0144680 A1* | 6/2010 | Skulachev et al. ........... | 514/125 |
| 2010/0234326 A1* | 9/2010 | Skulachev et al. ........... | 514/125 |
| 2010/0292625 A1* | 11/2010 | Skulachev et al. ........... | 602/50 |
| 2010/0323992 A1* | 12/2010 | Skulachev et al. ........... | 514/125 |
| 2011/0077159 A1* | 3/2011 | Skulachev et al. ........... | 504/207 |

FOREIGN PATENT DOCUMENTS

| | | |
|---|---|---|
| EP | 1047701 B1 | 5/2005 |
| EP | 1534720 A1 | 6/2005 |
| EP | 1321138 B1 | 4/2006 |
| RU | 2318500 C2 | 3/2008 |
| WO | 9926582 A2 | 6/1999 |
| WO | 2004/014927 A1 | 2/2004 |
| WO | 2006/005759 A2 | 1/2006 |
| WO | 2007046729 A1 | 4/2007 |
| WO | 2008/048134 A1 | 4/2008 |
| WO | 2009/005386 A1 | 1/2009 |
| WO | 2009/158348 A1 | 12/2009 |

OTHER PUBLICATIONS

Stella et al. Prodrugs: Challenges and Rewards, Springer New York 2007.*
Rodriguez-Spong, B. et al. Advanced Drug Delivery Reviews 2004, 56, 241-274.*
Johnson L. V. et al. Proc. Natl. Acad. Sci. USA 1980, 77 (2), 990-994.*
Gear et al. J. Biol. Chem. 249, 11, 3628-3637.*
Murphy M. P. Trends in Biotechnology 1997, 15 (8), 326-330.*
Barclay et al. Phenols as antioxidants. In the Chemistry of Phenols, Part 2, Rappoport, Z., Ed., Willey, 2003, pp. 875.*
Kirkinezos et al. Seminars in Cell & Developmental Biology 2001, 12, 449-457.*
Stella et al. Prodrugs: Challenges and Rewards, Springer New York, 2007.*
Rodriguez-Spong et al. Advanced Drug Delivery Reviews 2004, 56, 241-274.*
Johnson et al. Proc. Natl. Acad. Sci. USA 1980, 77 (2), 990-994.*
Gear, A. R. L. J. Biol. Chem. 1974, 249 (11), 3628-3637.*
Murphy, M. P. Trends in Biotechnology 1997, 15 (8), 326-330.*
PubChem compound CID 388445; Mar.26, 2005 [retrieved from http://pubchem.ncbi.nlm.nih.gov/summary/summary.cgi?cid=38845&loc=ec_rcs on Jul. 31, 2012] whole doc (4 pages).
International Search Report and Written Opinion of the International Searching Authority, PCT/US12/40711, Aug. 20, 2012 (8 pages).
Adlam et al., "Targeting an antioxidant to mitochondria decreases cardiac ischemia-reperfusion injury," FASEB J., 19:1088-1095 (2005).
Becker, "New concepts in reactive oxygen species and cardiovascular reperfusion physiology," Cardiovascular Research, 61:461-470 (2004).
Bernard et al., "The Hytopthermia after cardiac arrest study group. Mild therapeutic hypothermia to improve the neurologic outcome after cardiac arrest," N. Engl. J. Med. 346(8):549-556 (2002).
Collins et al., "Heart protection study collaborative group. Effects of cholesterol-lowering with simvastatin on stroke and other major vascular events in 20,536 people with cerebrovascular disease or other high-risk conditions," Lancet 363:757-767 (2004).
Demougeot et al., "Cytoprotective efficacy and mechanisms of the liposoluble iron chelator 2,2'-dipyridyl in the rat photothrombotic ischemic stroke model," J. Pharmacol. Experiment. Thera., 311(3):1080-1087 (2004).
Faa et al., "Iron chelating agents in clinical practice," Coordination Chemistry Reviews, 184:291-310 (1999).

(Continued)

*Primary Examiner* — Sreeni Padmanabhan
*Assistant Examiner* — Irina Neagu
(74) *Attorney, Agent, or Firm* — Ann-Louise Kerner; K&L Gates LLP (57) ABSTRACT

The invention relates to pharmacology and medicine, in particular to a class of mitochondrially-addressed compounds which can be used in the pharmaceutical compositions of medicinal agents (preparations) for preventing and treating cardiovascular diseases and diseases and pathological conditions caused by disturbed blood circulation or oxygen supply to tissues and organs.

5 Claims, 8 Drawing Sheets

(56) References Cited

OTHER PUBLICATIONS

Kirschner et al., "Role of iron oxygen-derived free radicals in ischemia-reperfusion injury" J. Am. Coll. Surg., 179:103-117 (1994).
Kromhout, "Diet and cardiovascular diseases," J. Nutr. Health Aging, 5(3):144-149 (2001).
Kutala et al., "Prevention of postischemic myocardial reperfusion injury by the combined treatment of NCX-4016 and Tempol.," J. Cardiovasc. Pharmacol., 48(3):79-87 (2006).
Petrosillo et al., "Protective effect of melatonin against mitochondrial dysfunction associated with cardiac ischemia-reperfusion: role of cardiolipin," FASEB J., 20:269-276 (2006).
Petrosillo et al., "Mitochondrial dysfunction associated with cardiac ischemia/reperfusion can be attenuated by oxygen tension control. Role of oxygen-free radicals and cardiolipin," Biochimica et Biophysica Acta, 1710:78-86 (2005).
Riess et al., "Reduced reactive O2 species formation and preserved mitochondrial NADH and [Ca2+] levels during short-term 17° C ischemia in intact hearts," Cardiovasc. Res., 61:580-590 (2004).
Spencer et al., "Transition metal chelators reduce directly measured myocardial free radical production during reperfusion," J. Cardiovasc. Pharmacol. 32(3):343-348 (1998).
Tompkins et al., "Mitochondrial dysfunction in cardiac ischemia-reperfusion injury: ROS from complex I, without inhibition," Biochimica et Biophysica Acta, 1762:223-231 (2006).
Vanden Hoek et al., "Reperfusion injury in cardiac myocytes after simulated ischemia," Am. J. Phys., 270:H1334-H1341 (1996).
Zweier et al., "Direct measurement of free radical generation following reperfusion of ischemic myocardium," PNAS USA, 84:1404-1407 (1987).
International Search Report and Written Opinion of the International Searching Authority, PCT/RU2007/000355, Mar. 27, 2008 (10 pages).
Longo et al. (2005) "Programmed and altruistic ageing," Nature Reviews Genetics, 6:866-872.
Agapova et al. (2008) "Mitochondria-Targeted Plastoquinone Derivatives as Tools to Interrupt Execution of the Aging Program. 3. Inhibitory Effect of SkQ1 on Tumor Development From p53-Deficient Cells," Biochem. (Mosc)., 73 (12):1300-1316 (+ 3 fig. pages).
Anisimov (2007) "Molecular and Physiological Mechanisms of Aging," Antioksidanty, Nov. 27, 2007, [on line] http://imquest.alfaspace.net/BOOK/MFMA/mfma_3_9_2.htm?embedded=yes translated from Russian to English.
Antonenko et al. (2008) "Mitochondria-Targeted Plastoquinone Derivatives as Tools to Interrupt Execution of the Aging Program. 1. Cationic Plastoquinone Derivatives: Sythesis and in vitro Studies," Biochemistry (Moscow), 73(12) 1273-1287.
Antonenko et al. (2008) "Protective effects of mitochondria-targeted antioxidant SkQ in aqueous and lipid membrane environments," J. Membr. Biol., 222:141-149.
Holloszy (1998) "Longevity of exercising male rats: effect of an antioxidant supplemented diet," Mechanisms of Ageing and Development, 100:211-219.
Berge et al. (1977) "Pharmaceutical Salts," J. Pharma. Sci., 66(1):1-19.
Blaikie et al. (2006) "Targeting Dinitrophenol to Mitochondria: Limitations to the Development of a Self-limiting Mitochondrial Protonophore," Biosci. Rep., 26:231-243.
Brand et al. (1992) "The mechanism of the increase in mitochondrial proton permeability induced by thyroid hormones," Eur. J. Biochem. 206:775-781.
Doughan et al. (2007) "Original Research Communication: Mitochondrial Redox Cycling of Mitoquinone Leads to superoxide Production and Cellular Apoptosis," Antioxid. & Redox Signal., 9(11):1825-1836.
Kasahara, et al. (2005) "Manganese Superoxide Dismutase protects against oxidation-induced apoptosis in mouse retinal pigment epithelium: implications for age-related macular degeneration," Author Manuscript, NIH Public Access PMC Nov. 1, 2005 : 1-18, Invest. Ophthalmol. Vis. Sci., 46(9):3426-3434.

Green et al. (2004) "Prevention of Mitochondrial Oxidative Damage as a Therapeutic Strategy in Diabetes," Diabetes, 53(1):S110-S118.
Hansford et al. (1997) "Dependence of H2O2 formation by rat heart mitochondria on substrate availability and donor age," J. Bioenerg. Biomem. 29(1):89-95.
Havens et al. (2006) "Regulation of Late G1/S Phase Transition and APCCdh1 by Reactive Oxygen Species," Mol. Cell. Biol., 26(12):4701-4711.
Clem et al. (2008) "Small-molecule inhibition of 6-phosphofructo-2-kinase activity suppresses glycolytic flux and tumor growth," Mol. Canc. Ther. 7(1):110-120.
King et al. (2004) "Mitochondria-derived reactive oxygen species mediate blue light-induced death of retinal pigment epithelial cells," Photochem. and Photobiol., 79(5):470-475.
Liu et al. (1993) "Age-associated changes in superoxide dismutase activity, thiobarbituric acid reactivity and reduced glutathione level in the brain and liver in senescence accelerated mice (SAM): a comparison with ddY mice," Mech. Ageing & Dev., 71:23-30.
Li et al. (2000) "Skeletal muscle respiratory uncoupling prevents diet-induced obesity and insulin resistance in mice," Nat. Med. 6(10):1115-1120.
Sheu et al. (2006) "Targeting antioxidants to mitochondria: a new therapeutic direction," Biochimica et Biophysica Acta, 1762:256-265.
Goldstein (2002) "Reactive oxygen species as essential components of ambient air," Biochemistry (Mosc.) 67:161-170.
Lou et al. (2007) "Mitochondrial Uncouplers With an Extraordinary Dynamic Range," Biochem. J., 407:129-140.
Reddy (2006) "Mitochondrial oxidative damage in aging and Alzheimer's disease: implications for mitochondrially targeted antioxidant therapeutics," J. Biomedicine and Biotech., Art.ID 31372:1-13.
Neroev et al. (2008) Mitochondria-Targeted Plastoquinone Derivatives as Tools to Interrupt Execution of the Aging Program. 4. Age-Related Eye Disease. SkQ1 Returns Vision to Blind Animals, Biochemistry (Mosc.), 73 (12):1317-1328.
Popova et al. (2006) "MitoQ induced miofibroblast differentiation of human fibroblasts," Biochimica et Biophysica Acta, S:433-434.
Papp et al. (1999) "Glutathione status in retinopathy of prematurity," Free Radic. Biol. & Med., 27(7-8):738-743.
Petrosillo et al. (2005) "Mitochondrial dysfunction associated with cardiac ischemia/reperfusion can be attenuated by oxygen tension control. Role of oxygen-free radicals and cardiolipin," Biochimica et Biophysica Acta, 1710:78-86.
Petrosillo et al. (2006) "Protective effect of melatonin against mitochondrial dysfunction associated with cardiac ischemia-reperfusion: role of cardiolipin," FASEB J., 20:269-276.
Skulachev (2007) "A Biochemical Approach to the Problem of Aging: 'Megaproject' on Membrane-Penetrating Ions. The First Results and Prospects," Biochem. (Moscow), 72(12):1385-1396.
Popova et al. (2010) "Scavenging of Reactive Oxygen Species in Mitochondria Induces Myofibroblast Differentiation," Antiox. & Redox. Signal., 13(9):1297-1307.
Pozniakovsky et al. (2005) "Role of mitochondria in the pheromone- and amiodarone-induced programmed death of yeast, "J. Cell Biol., 168(2):257-69.
Sundaresan et al. (1995) "Requirement for Generation of H2O2 for Platelet-Derived Growth Factor Signal Transduction," Science, 270:296-299.
Bakeeva et al. (2008) "Mitochondria-targeted plastoquinone derivatives as tools to interrupt execution of the aging program. 2. Treatment of some ROS- and Age-related diseases (heart arrhythmia, heart infarctions, kidney ischemia, and stroke)," Biochemistry (Moscow), 73(12):1288-1299 and 1 figure.
Sidorova et al. (2004) "Transcriptional activation of cytochrome P450 1A1 with alpha-tocopherol," Bull Exp. Bio. Med., 138(3):233-236.
Yildirim et al. (2005) "Role of oxidative stress enzymes in open-angle glaucoma," Eye, 19:580-583.
Reliene et al. (2007) "Antioxidants suppress lymphoma and increase longevity in atm-deficient mice," J. Nutrition, 137:229S-232S.
Green (1974) "The electromechanochemical model for energy coupling in mitochondria," Biochimica et Biophysica Acta, 346:27-78.

Skulachev (2005) "Critical Review: How to Clean the Dirtiest Place in the Cell: Cationic Antioxidants as Intramitochondrial ROS Scavengers," IUBMB Life, 57(415):305-310.

Kirste et al. (1995) "Continuous-wave electron spin resonance studies of porphyrin and porphyrin-quinone triplet states," J. Chem. Soc. Perkin Trans. 2:2147-2152.

Murphy et al. (2007) Targeting antioxidants to mitochondria by conjugation to lipophilic cations. Annu. Rev. Pharmacol. Toxicol., 47:629-656.

Starkov et al. (1997) "6-ketocholestanol is a recoupler for mitochondria, chromatophores and cytochrome oxidase proteoliposomes," Biochim. Biophys. Acta. 1318:159-172.

Skulachev (2003) "Aging and the programmed death phenomena," Topics in Current Genetics, vol. 3, Nystrom and Osiewacz, Eds., Model systems in Aging, Springer-Verlag Berlin Heidelberg 191-238.

Skulachev et al. (2009) "An attempt to prevent senescence: a mitochondrial approach," Biochimica et Biophysica Acta., 1787:437-461.

Smith et al. (2008) "Mitochondria-targeted antioxidants in the treatment of disease,"Ann. N.Y. Acad. Sci., 1147:105-111.

Snow et al. (2010) "A double-blind, placebo-controlled study to assess the mitochondria-targeted antioxidant MitoQ as a disease-modifying therapy in Parkinson's disease," Mov. Disord. 25(11):1670-1674.

Stefanova et al. (2010) "Behavioral effects induced by mitochondria-targeted antioxidant SkQ1 in Wistar and senescence-accelerated OXYS rats," J. Alzheimer's Dis. 21:479-491.

Triet et al. (1993) "Anxiogenic stimuli in the elevated plus-maze," Pharmacol. Biochem. & Behav. 44:463-469.

Mecocci et al. (2000) "Plasma antioxidants and longevity: a study on healthy centenarians," Free Radical Biology and Medicine, 28(8):1243-1248.

Orr et al. (2003) "Effects of overexpression of copper-zinc and manganese superoxide dismutases, catalase, and thioredoxin reductase genes on longevity in *Drosophila melanogaster*," J. Biol. Chem., 278(29):26418-26422.

Plotnikov et al. (2008) "Interrelations of Mitochondrial Fragmentation and Cell Death Under Ischemia/Reoxygenation and UV-Irradiation: Protective Effects of SkQ1, Lithium Ions and Insulin," FEBS Letters, 582:3117-3124.

Plotnikov et al. (2010) "New-generation Skulachev ions exhibiting nephroprotective and neuroprotective properties." Biochemistry (Mosc.), 75(2):145-150.

Skulachev et al. (2005) "Aging as mitochondria-mediated atavistic program. Can aging be switched off?" Ann. N.Y. Acad. Sci., 1057:145-164.

Tauskela (2007) "MitoQ—a mitochondria-targeted antioxidant," IDrugs, 10:399-412.

PCT International Search Report and Written Opinion of the International Searching Authority for PCT Application No. PCT/RU2006/000546, mailed Jul. 5, 2007, 14 pages.

PCT International Search Report mailed Nov. 1, 2007 and International Preliminary Report on Patentability issued Aug. 4, 2009 for PCT Application No. PCT/RU2007/000043, 9 pages.

International Search Report and Written Opinion of the International Searching Authority, PCT/RU2009/000295, Feb. 25, 2010, 7 pages.

International Search Report and Written Opinion, PCT/RU2006/000547, dated Jul. 5, 2007 (7 pages).

International Search Report and Written Opinion, PCT/RU2006/000394, dated Nov. 2, 2006 (6 pages).

International Search Report dated Dec. 20, 2007 and International Preliminary Report on Patentability dated Nov. 10, 2009, PCT/RU2007/000171 (16 pages).

International Search Report, PCT/RU2008/000706, Aug. 13, 2009 (3 pages).

International Search Report and Written Opinion of the International Searching Authority, PCT/RU2007/000044, Nov. 1, 2007, 9 pages.

International Search Report and Written Opinion, PCT/RU2009/000621, dated Aug. 12, 2010 (12 pages).

* cited by examiner

USE OF MITOCHONDRIALLY-ADDRESSED COMPOUNDS FOR PREVENTING AND TREATING CARDIOVASCULAR DISEASES

FIELD OF THE INVENTION

The invention relates to pharmacology and medicine, in particular to a class of chemical compounds of structure (I) which can be used in the pharmaceutical compositions of medicinal agents (preparations) for preventing and treating cardiovascular diseases as well as diseases and pathological conditions caused by disorders of blood circulation or oxygen supply to tissues and organs.

BACKGROUND OF THE INVENTION

In today's world, cardiovascular diseases are the leading cause of death (29% of all deaths in 2002 (The world health report 2004)): hypertension and stroke (one of its most severe complications), atherosclerosis, ischemic brain disease (which is in most cases caused by atherosclerosis), and finally, ischemic heart disease and acute myocardial infarction (as its manifestation).

In a broad sense, infarction implies necrosis of part of organ due to insufficiency of blood supply, or mechanical or bacterial/viral lesions. Usually, infarction is a consequence of ischemia—the situation in which a lumen-bearing blood vessel becomes narrowed due to atherosclerotic plaque, or a vessel becomes obstructed by a thrombus or compressed by any entity (e.g., cyst or tumor). According to WHO estimates, ischemic heart disease and its consequences resulted in 12.6% of deaths in 2002 (The world health report 2004). In industrialized countries, this proportion is even higher—30%.

Anti-ischemic measures include several interrelated stages: prevention of ischemia or its treatment and prevention of its most severe consequences, such as infarction. The prevention includes reduction of risk factors, primarily atherosclerosis development: smoking cessation, reduction the level of low density lipoproteins (LDL) in the blood, diet, lifestyle, etc. In the development of ischemia, the primary goal is to restore blood supply (reperfusion) of tissue within 1.5-2 hours after onset of ischemia, and for that purpose, vasodilators (e.g., nitroglycerin), anticoagulants (aspirin, heparin), thrombolytic agents, beta-adrenergic blockers relieving stress and reducing oxygen demand in ischemic tissue, oxygen therapy, and finally, surgical methods, such as angioplasty, bypass surgery, etc. are used.

Reperfusion of tissue, especially after long-term ischemia, is accompanied by the accumulation of reactive oxygen species (ROS) (J. L. Zweier, J. T. Flaherty, M. L. Weisfeldt. Direct measurement of free radical generation following reperfusion of ischemic myocardium. 1987, PNAS USA, 84, 1404-1407). During ischemia, the partial pressure of oxygen in cells decreases, electron carriers of the mitochondrial respiratory chain are reduced that leads to enhanced generation of reactive oxygen species (superoxide anion radical at first, then hydrogen peroxide), accompanied by transition of iron atoms from the ferric state ($Fe^{3+}$) to the ferrous states ($Fe^{2+}$). This facilitates the Fenton reaction, thus generating a powerful oxidant, the OH* radical. Neutrophils attracted to the ischemic focus also actively release superoxide and hydrogen peroxide on the background of increased oxygen delivery during reperfusion.

All this leads to the activation of free-radical oxidation (A. J. Tompkins, L. S. Burwell, S. B. Digemess, C. Zaragoza, W. L. Holman and P. S. Brookes. Mitochondrial dysfunction in cardiac ischemia-reperfusion injury: ROS from complex I, without inhibition. 2006, Biochim Biophys Acta. 1762, 2, 223-231), and as a consequence, the development of oxidative stress. The latter leads to consequences which are often more severe than ischemic blood circulatory disorders per se (Vanden Hoek T L, Shao Z, Li C, Zak R, Schumacker P T, Becker L B. Reperfusion injury in cardiac myocytes after simulated ischemia. 1996, Am. J. Phys., 270, 1334-1341). Free radicals have a direct damaging effect on intracellular protein structures, nucleic acids, as well as various membranes; peroxidation of polyunsaturated fatty acids embedded in the membranes, in turn, disturbs the barrier properties of the membranes and leads to perturbed ion homeostasis (in the case of reperfused heart muscle, lipid peroxidation and the peroxidation-induced ion imbalance are considered as one of the leading causes of reperfusion cardiac arrhythmias). In addition, free radical compounds initiate vasoconstriction and hypercoagulability, and accelerated degradation of NO which mediates vasorelaxant (in this situation—anti-ischemic) action.

Namely ROS are considered to be one of the key factors triggering the mechanism of necrosis and apoptosis in ischemic tissue. Therefore, preventing the synthesis of mitochondrial ROS or neutralization of the latter is critical for survival or recovery of the function of ischemic tissue cells.

Attempts to reduce reperfusion-induced oxidative stress in ischemic tissue were made repeatedly. For example, local hypoxia—reduction of perfusate oxygen content entering the ischemic heart during the first few minutes of reperfusion, suppressed ROS generation and had a protective effect on mitochondria (G. Petrosillo, N. Di Venosa, F. M. Ruggiero, M. Pistolese, D. D'Agostino, E. Tiravanti, T. Fiore, G. Paradies. Mitochondrial dysfunction associated with cardiac ischemia/reperfusion can be attenuated by oxygen tension control. Role of oxygen-free radicals and cardiolipin. 2005, Biochimica et Biophysica Acta, 1710, 78-86).

When ischemic tissue is subjected to hypothermic conditions, ROS production is also reduced, the consequences of ischemia are mitigated, thereby increasing time period during which the tissue can remain under ischemic condition without irreversible changes during the subsequent reperfusion (Riess M. L., Camara A. K. S., Kevin L. G., An J., Stowe D. F. Reduced reactive $O_2$ species formation and preserved mitochondrial NADH and [$Ca^{2+}$] levels during short-term 17° C. ischemia in intact hearts. 2004, Cardiovascular Research, 61, 580-590). A positive clinical effect of hypothermia was also observed (Hypothermia After Cardiac Arrest Study Group. Mild therapeutic hypothermia to improve the neurologic outcome after cardiac arrest, 2002, New Engl. J. Med., 346, 8, 549-56). However, the clinical applicability of the said method—as well as said local hypoxia—is very limited, primarily because of technical difficulties.

Another way to mitigate the damage caused by ischemia and reperfusion is the use of chelating agents binding free ferrous iron; accumulation of $Fe^{2+}$ ions in ischemic tissue is one of the factors stimulating a surge in ROS synthesis during reperfusion (the Fenton reaction which occurs with hydroxyl radical formation).

It was shown that the use of chelating agents inhibits ROS synthesis during reperfusion (Spencer K T, Lindower P D, Buettner G R, Kerber R E. Transition metal chelators reduce directly measured myocardial free radical production during reperfusion. 1998, J. Cardiovasc Pharmacol, 32, 3, 343-348), reduces infarct size (C. Demougeot, M. Van Hoecke, N. Bertrand, A. Prigent-Tessier, C. Mossiat, A. Beley, and C. Marie. Cytoprotective Efficacy and Mechanisms of the Liposoluble Iron Chelator 2,2_-Dipyridyl in the Rat Photothrombotic Ischemic Stroke Model. 2004, The Journal of Pharmacology and Experimental Therapeutics, 311, 1080-1087). However, it should be noted that the clinical use of chelating agents is limited since they can cause side effects: for example, long-term use of iron ion chelator such as deferoxamine (especially by young people) can lead to stunted growth, speech disorder, hearing loss, disorder of skeletal formation ((Faa G., Crisponi G. Iron chelating agents in clinical practice. 1999, Coordination Chemistry Reviews, 184, 1, 291-310), heart malfunction and hypotension (Kirschner R E, Fantini G A. Role of iron oxygen-derived free radicals in ischemia-reperfusion injury. 1994b J. Am. Coll. Surg., 179, 103-117).

Finally—since the case in point is ROS-induced damage—it would be logical to assume that preparations with antioxidant effect may also reduce the risk of myocardial infarction and to mitigate the severity of other adverse effects in ischemic tissue. Indeed, it was shown (Kutala V K, Khan M, Mandal R., Potaraju V., Colantuono G., Kumbala D, Kuppusamy P. Prevention of Postischemic Myocardial Reperfusion Injury by the Combined Treatment of NCX-4016 and Tempol. 2006, J Cardiovasc Pharmacol., 48, 3, 79-87), that pre-perfusion of rat heart with antioxidant Tempol reduced infarct size caused by subsequent ischemia/reperfusion by 1.5 times, and the combination of Tempol and NCX-4016 (NO donor)—by almost 2 times. Reduction of ROS production and protection of membrane lipids in ischemic heart mitochondria from peroxidation by means of antioxidant melatonin was demonstrated by Petrosillo et al. (Petrosillo G, Di Venosa N, Pistolese M, Casanova G, Tiravanti E, Colantuono G, Federici A, Paradies G, Ruggiero F. M. Protective effect of melatonin against mitochondrial dysfunction associated with cardiac ischemiareperfusion: role of cardiolipin. 2006, The FASEB Journal, 20, 269-276).

At the same time, attempts to achieve the effect of preventing the development of ischemic processes by means of specialized vitamins-antioxidants (vitamins C, E and beta-carotene), failed to reveal clinical relevance of such prevention (Collins R, Armitage J, Parish S, Sleight P, Peto R; Heart Protection Study Collaborative Group. Effects of cholesterol-lowering with simvastatin on stroke and other major vascular events in 20536 people with cerebrovascular disease or other high-risk conditions. 2004, Lancet, 363, 9411, 757-767). In a review (Kromhout D. Diet and cardiovascular diseases. 2001, J. Nutr. Health Aging, 5, 144-149) on the same issue, similar conclusions were made: convincing clinical evidence for the ability of antioxidants, vitamins E and C as well as carotenoides, to prevent the development of ischemic heart disease was not obtained.

The apparent contradiction between the encouraging results of the experiments on cell cultures or isolated organs, on the one hand, and the disappointing clinical trial data—on the other hand, may be partly explained by "the problem of delivery". Antioxidant therapy should be conducted at the beginning of reperfusion, the start time of which, in turn, is critical to prevent or minimize the development of myocardial infarction. Antioxidant must not only be promptly delivered to the ischemic region—its intracellular localization is also important. It is possible that namely the inability of existing antioxidant preparations to be quickly and selectively transported into mitochondria, the ROS generation site, is the cause of the low efficiency of such preparations in clinical practice (Becker L. B. New concepts in reactive oxygen species and cardiovascular reperfusion physiology. 2004, Cardiovascular Research, 61, 461-470).

For delivery of antioxidants to mitochondria, a strategy with two different mechanisms of its implementation can be applied. The strategy is based on transport of a required antioxidant to mitochondria which is conjugated with elements transported to the mitochondrial matrix. The nature of these elements is twofold—these can be either penetrating lipophilic cations which can be spontaneously transported along the electric field created on the inner mitochondrial membrane, or signal peptide sequences being part of the transported peptides, after their processing the mature protein is brought into the correct mitochondrial compartment.

To date, very limited number of biologically active compounds is known which can be targeted to mitochondria at the expense of energy of electrochemical potential of hydrogen ions. Among these are mitochondria-targeted antioxidant MitoQ and its variants (MitoQ5, MitoQ3). The said substances are ubiquinol (the reduced form of ubiquinone) attached to triphenylphosphonium through C-10 linker group (C-5, C-3, respectively). In description of the invention U.S. Pat. No. 6,331,532, MitoQ is claimed to be an active compound of compositions intended for the treatment and prevention of diseases associated with oxidative stress. Another compound, mitochondria-targeted mimetic of glutathione peroxidase ebselen is claimed in the claims of invention U.S. Pat. No. 7,109,189 as treatment for adverse effects of reperfusion of ischemic tissue, infarction and as preparation applicable in surgery and transplantation. However, the authors of said invention did not provide any experimental data supporting the possibility of such use of ebselen, since data on the antioxidant properties of ebselen were obtained in experiments on isolated mitochondria and mitochondrial membranes.

Adlam et al. shows an example of the effect of MitoQ observed in an experiment where rats were fed the said compound for 14 days, with subsequent study of the properties of their isolated hearts perfused by Langendorfs method and exposed to ischemia/reperfusion. Said data indirectly confirm the statement that MitoQ can be used for prevention or treatment of ischemic myocardial damage. However, normothermal ischemia followed by reperfusion used by the authors of the said work has all the limitations of in vitro model. Also, given the apparent lack of reliable statistics to assess the number of experiments (6 animals in each group), it remains unclear how much do the average values obtained characterize the changes in the restoration of cardiac function associated with the chemical structure of antioxidants, rather than differences in the development of arrhythmias.

Summarizing this section, one can conclude that at present there is no clinically applicable and experimentally confirmed scheme of treatment and prevention of heart diseases by means of mitochondria-targeted antioxidants.

DESCRIPTION OF THE INVENTION

One aspect of the present invention is a new application of a pharmaceutical composition of mitochondria-targeted antioxidants (i.e., compounds of structure (I)) to produce medicinal preparations that are intended for the prevention and treatment of cardiovascular pathologies, as well as diseases and pathological conditions originating from disorders of blood circulation or oxygen supply to tissues and organs.

Said composition comprises compounds that include targeting moiety, linker group and antioxidant, and the general chemical structure of these compounds can be described by the following structure (I):

(I)

wherein:
A is the effector moiety—antioxidant:

and/or reduced form thereof, wherein:
m is an integer from 1 to 3;
each Y is independently selected from the group consisting of: lower alkyl, lower alkoxy; or two adjacent Y groups, together with carbon atoms to which they are attached, form a following structure:

and/or reduced form thereof
wherein R1 and R2 may be the same or different and are each independently lower alkyl or lower alkoxy;
L is a linker group, comprising:
a) straight or branched hydrocarbon chain which can be optionally substituted by one or more substituents and optionally contains one or more double or triple bonds; or
b) natural isoprene chain;
n is integer from 1 to 20;
B—targeting group comprising Skulachev-ion Sk:
$Sk^+Z^-$
where Sk—lipophilic cation, Z—pharmacologically acceptable anion;
with proviso that in compound of structure (I) A is not ubiquinone (e.g., 2-methyl-4,5-dimethoxy-3,6-dioxo-1,4-cyclohexadienyl) or tocopherol or mimetic of superoxide dismutase or ebselen; while L—divalent decyl or divalent pentyl or divalent propyl radical; and while B is triphenylphosphonium cation;
or solvates, isomers, prodrugs; or pharmacologically acceptable salts thereof.

Another aspect of the present invention is the use of a pharmaceutical composition for manufacturing medicinal preparations that are intended for the prevention and treatment of cardiovascular pathologies, including atherosclerosis, cardiac arrhythmias, ischemic heart disease, cardiac infarction, renal ischemia or infarction, stroke, as well as diseases and pathological conditions originating from disorders of blood circulation or oxygen supply to tissues and organs.

One more aspect of the present invention is the use of a pharmaceutical composition for treatment of pathological conditions that are consequences of nonischemic blood circulation disorders, including the consequences of hemorrhagic hypovolemia caused by destruction of vessels or violation of their permeability as well as hypovolemia caused by vasodilators.

Another aspect of the present invention is the use of a pharmaceutical composition for treatment of pathological conditions that are consequences of nonischemic blood circulation disorders, including hypovolemia caused by loss of water through the skin, lungs, gastrointestinal tract or kidneys, including hypovolemia provoked by diuretics.

One more aspect of the present invention is the use of a pharmaceutical composition for treatment of consequences of hypoxic hypoxia caused by a lack of oxygen in arterial blood, including hypoxia caused by a lack of oxygen in inhaled air.

Another aspect of the present invention is the use of a pharmaceutical composition for treatment of consequences of anemic hypoxia caused by decrease in oxygen capacity of blood due to a fall in hemoglobin content or change in its state.

One more aspect of the present invention is the use of a pharmaceutical composition for the prevention or treatment of unwanted changes in cells, tissues or organs in which natural blood circulation and oxygen supply are limited or terminated during medical intervention, including apheresis, reducing or eliminating blood supply to cells, tissues or organs to the purpose of their further conservation and/or transplantation as well as various surgical operations.

Ischemic heart disease is considered to mean: angina pectoris, unstable angina, unstable angina with hypertension, angina pectoris with documented spasm, angina pectoris with documented spasm with hypertension, acute myocardial infarction, acute transmural anterior wall myocardial infarction, acute transmural anterior wall myocardial infarction with hypertension, acute transmural inferior wall myocardial infarction, acute transmural inferior wall myocardial infarction with hypertension, acute subendocardial myocardial infarction, acute subendocardial myocardial infarction with hypertension, myocardial reinfarction, inferior wall myocardial reinfarction, some current complications of acute myocardial infarction, and hemopericardium as complication following acute myocardial infarction, atrial septal defect as current complication of acute myocardial infarction, ventricular septal defect as current complication of acute myocardial infarction, atrial thrombosis, auricular thrombosis and ventricular thrombosis as current complications of acute myocardial infarction, other forms of acute ischemic heart disease, coronary thrombosis which does not lead to myocardial infarction, Dressler's syndrome, Dressler's syndrome with hypertension, chronic ischemic heart disease, atherosclerotic cardiovascular disease, previous experience of myocardial infarction, cardiac aneurysm, cardiac aneurysm with hypertension, coronary artery aneurysm, coronary artery aneurysm with hypertension, ischemic cardiomyopathy, asymptomatic myocardial ischemia.

Other heart diseases are considered to mean: acute pericarditis, acute nonspecific idiopathic pericarditis, infectious pericarditis, chronic adhesive pericarditis, chronic constrictive pericarditis, non-inflammatory pericardial effusion, acute and subacute endocarditis, acute and subacute infective endocarditis, non-rheumatic mitral valve lesions, mitral valve insufficiency, mitral valve prolapse, non-rheumatic mitral valve stenosis, non-rheumatic aortic valve lesions, aortic valve stenosis, aortic valve insufficiency, non-rheumatic tricuspid valve lesions, non-rheumatic tricuspid valve stenosis, non-rheumatic tricuspid valve insufficiency, pulmonary valve lesions, pulmonary valve stenosis, pulmonary valve insufficiency, pulmonary valve stenosis with insufficiency, acute myocarditis, infectious myocarditis, isolated myocarditis, cardiomyopathy, dilated cardiomyopathy, hypertrophic obstructive cardiomyopathy, endomyocardial (eosinophilic) disease, endocardial fibroelastosis, alcoholic cardiomyopathy, cardiomyopathy caused by medicinal agents and other external factors, atrioventricular block and left His' bundle block, first-degree atrioventricular block, second-degree atrioventricular block, complete atrioventricular block, pre-excitation syndrome, cardiac arrest, cardiac arrest with successful restoration of cardiac activity, paroxysmal tachycardia, recurrent ventricular arrhythmia, supraventricular tachycardia, ventricular tachycardia, atrial fibrillation, atrial flutter, ventricular fibrillation, ventricular flutter, premature atrial depolarization, premature ventricular depolarization, sick sinus syndrome, heart failure, congestive heart failure, left ventricular failure, myocardial degeneration.

Stroke is considered to mean hemorrhagic stroke, ischemic stroke, and their symptoms.

Renal ischemia or renal infarction is considered to mean: periarteritis nodosa, Wegener's granulomatosis, hemolytic-uremic syndrome, idiopathic thrombocytopenic purpura, disseminated intravascular coagulation syndrome (DIC syndrome), renal artery ischemia, or renal artery infarction (extrarenal part), renal arteriosclerosis, congenital renal stenosis, Goldblatt kidney, acute nephritic syndrome, minor glomerular disorders, focal and segmental glomerular lesions, diffuse membranous glomerulonephritis, diffuse mesangial proliferative glomerulonephritis, diffuse endocapillary proliferative glomerulonephritis, diffuse mesangiocapillary glomerulonephritis, rhabdomyolysis, dense deposit disease, diffuse crescentic glomerulonephritis, rapidly progressive nephritic syndrome, recurrent and persistent hematuria, chronic nephritic syndrome, nephrotic syndrome, nephritic syndrome.

Application of pharmaceutical compositions related to the present invention can be both somatic and local. Procedures of administration comprise enteral, such as oral, sublingual and rectal; local, such as transdermal, intradermal and oculodermal; and parenteral. Suitable parenteral procedures of administration comprise injections, for example, intravenous, intramuscular, subdermal, intraperitoneal, intraarterial, and other injections, and non-injecting practices, such as vaginal or nasal, as well as procedure of administration of a pharmaceutical composition in form of angioplastic stent coating. Preferably, compounds and pharmaceutical compositions related to the present invention are for intraperitoneal, intravenous, intraarterial, parenteral or oral administration. In particular, administration can be given in form of injections or tablets, granules, capsules or other pressed or compressed form.

When a compound of structure (I) is administered as a pharmaceutical composition, a compound of structure (I) should be mixed according to formula with a suitable amount of pharmacologically acceptable solvent or carrier so that to have the appropriate form for administration to a patient. The term "solvent" relates to diluent, auxiliary medicinal substance, filler or carrier which is mixed with a compound of structure (I) for administration to a patient. Liquids like water, and oils including petrolic, animal, vegetative and synthetic, such as peanut oil, soybean oil, mineral oil and other similar oils can be used as said pharmacological carriers. Normal saline solution, acacia pitch, gelatin, starch, tacl, keratin, colloid silver, urea etc can serve as said pharmacological solvents.

Said composition can also include auxiliary substances, stabilizers, thickeners, lubricant and coloring agents.

Compounds and compositions related to the present invention can be administered in form of capsules, tablets, pills, pillets, granules, syrups, elixirs, solutions, suspensions, emulsions, suppositories or retarded release substances, or in any other form suitable for administration to a patient. One aspect of the present invention is application of compounds of structure (I) and compositions in form of solutions for oral, intraperitoneal, intraarterial and intravenous administration.

Therapeutically justified amount of a compound of structure (I) required for treatment of a specific disease or symptom, depends on the nature of disease or symptom and a procedure of administration and should be determined at consultation with a physician in charge. Acceptable doses for oral administration are from 0.025 to 120000 microgram per kg of patient body weight, 25 microgram per kg of patient body weight is more preferable, and 50 microgram per kg of patient body weight is the most preferable. Acceptable doses for intravenous administration are from 0.1 to 10000 microgram per kg of patient body weight, 25 microgram per kg of patient body weight is more preferable, and 125 microgram per kg of patient body weight is the most preferable.

For optimal protection of cells, tissues and organs, a compound of structure (I) in form of a pharmaceutical composition is administered 6-48 hours (optimally—24 hours) prior to ischemic exposure.

Examples of Acceptable Pharmaceutical Compositions for Oral Administration:

Pharmaceutical composition—1—gelatin capsules:

| Ingredient | Amount (mg/capsule) |
| --- | --- |
| Compound of structure (I) | 0.0015-1000 |
| Starch | 0-650 |
| Starch powder | 0-650 |
| Liquid silicone | 0-15 |

Pharmaceutical composition—2—tablets:

| Ingredient | Amount (mg/capsule) |
| --- | --- |
| Compound of structure (I) | 0.0015-1000 |
| Microcrystalline cellulose | 200-650 |
| Silicon dioxide powder | 10-650 |
| Stearic acid | 5-15 |

Pharmaceutical composition—3—tablets:

| Ingredient | Amount (mg/capsule) |
| --- | --- |
| Compound of structure (I) | 0.0015-1000 |
| Starch | 45 |
| Microcrystalline cellulose | 35 |
| Polyvinylpyrrolidone (10% aqueous solution) | 4 |
| Carboxymethylcellulose, sodium salt | 4.5 |
| Talc | 1 |
| Magnesium stearate | 0.5 |

Pharmaceutical composition—4—suspensions:

| Ingredient | Amount (mg/5 ml) |
|---|---|
| Compounds of structure (I) | 0.0015-1000 |
| Syrup | 1.25 |
| Benzoic acid solution | 0.10 |
| Carboxymethylcellulose, sodium salt | 50 |
| Flavoring | By necessity |
| Coloring | By necessity |
| Distilled water | Up to 5 ml |

An example of acceptable pharmaceutical composition in the form of solution for intraperitoneal, intraarterial and intravenous administration (pH 6.5):

| Ingredient | Amount |
|---|---|
| Compound of structure (I) | 5 mg |
| Isotonic solution | 1000 ml |

An example of acceptable pharmaceutical composition for administration in the form of aerosol:

| Ingredient | Amount (weight percent) |
|---|---|
| Compound of structure (I) | 0.0025 |
| Ethanol | 25.75 |
| Difluorochloromethane | 70 |

An example of acceptable pharmaceutical composition for administration in the form of suppositories:

| Ingredient | Amount (mg/suppository) |
|---|---|
| Compound of structure (I) | 1 |
| Glycerides of saturated fatty acids | 2000 |

The following non-limiting Examples illustrate the preparation and use of compounds of structure I but should not be understood as limiting the invention as modifications in materials and methods will be apparent to the skilled person. The following examples should not be construed as limiting the scope of this disclosure.

These examples show that the correct use of compositions based on compounds of structure (I) can prevent or decelerate the development of pathological processes associated with ischemic blood circulation disorders in various organs including heart, kidney and brain.

EXAMPLES

1. Reduction of Myocardial Infarction Size in Rats after Regional Ischemia and Reperfusion in the Presence of SkQ1

To study a possibility of reduction of the irreversible damage of cardiomyocytes by SkQ1 in vivo a model of regional myocardial ischemia and reperfusion in anesthetized rats was used. Experiments were performed on Wistar male rats weighing 300-450 grams, fed a standard diet. In the control animals during three weeks received NaBr dissolved in 0.1 M phosphate buffer (pH 6.0), at a dose of 250 nmol/kg body weight/day. Animals of the experimental group during three weeks together with food received SkQ1 dissolved in 0.1 M phosphate buffer (pH 6.0), at a dose of 250 nmol/kg body weight/day.

In urethane-anesthetized animals (130 mg/kg body weight intraperitoneally administered), artificial ventilation of the lungs with room air with added oxygen at a rate of 60-80 beats per minute was carried out. Indicators of the acid-base balance of arterial blood (pH, $pO_2$ and $pCO_2$) during the entire experiment were controlled with the use of acid-base gas analyzer ABL-30 (Radiometer) and maintained at a physiological level.

Catheterization of the carotid artery was performed for recording arterial pressure (Mingograf 804, Siemens-Elema). The chest was opened by longitudinal dissection of the sternum and the heart was freed from the pericardium. To induce regional myocardial ischemia, the left ventricle was pierced with an atraumatic needle 5-0 under the left appendage in the direction perpendicular to long axis of the heart. Tightening the ligature at the anterior descending coronary artery (ADA) located deep in the pierced myocardium ceased blood supply to a portion of the myocardium, weakening of the ligature restored coronary flow.

The dissection is followed by a 30-min period of stabilization of hemodynamic parameters (the initial state). Then anterior descending coronary artery was occluded for 40 min followed by 60 min of reperfusion. At the end of the experiment, to identify the risk zone (RZ) and the intact zone, anterior descending coronary artery was occluded and a 2% Evans solution (2 ml) was injected as a bolus into the jugular vein. Then the heart was cut out and the left ventricle (LV) was separated and frozen at −20° C.

To measure infarct size, the method for histochemical localization of the risk zone (RZ) and myocardial infarction (MI) by tissue staining with 2,3,5-triphenyltetrazolium chloride (TFT) was used (Kitakaze M., Takashima S., Funaya H., Minamino T., Node K., Shinozaki Y., Mori H., Hori M., 1997. Temporary acidosis during reperfusion limits myocardial infarct size. *Am. J. Physiol.*; 272: H2071-H207). Cross-sections with a thickness of about 1.5-2 mm were prepared from the left ventricle, which were then incubated for 10 min in 1% TFT solution in 0.1 M phosphate buffer (pH 7.4 at 37° C.). The obtained samples were scanned, MI and RZ sizes were determined by the method of computer-assisted planimetry using the Imagecal program. Then the sections were weighed to determine LV mass. In each group, the risk zone/weight of the left ventricle (RZ/LV) and the myocardial infarction/risk zone (MI/RZ) ratios were estimated (Pisarenko O. I., Studneva I. M., Serebriakova L. I., Tskitishvili O. V., Timoshin A. A. Protection of rat heart myocardium with a selective $Na^+/H^+$ exchange inhibitor and ischemic preconditioning. Kardiologiia (in Russian). 2005; 45 (2): 37-44).

It was shown that in the initial state the mean arterial blood pressure (BP) in all groups tested was 98±5 mm Hg. Art., heart rate (HR)—223±6 beats/sec. No effect of SkQ1 on blood pressure and heart rate was observed in the experimental group.

Figure 1:
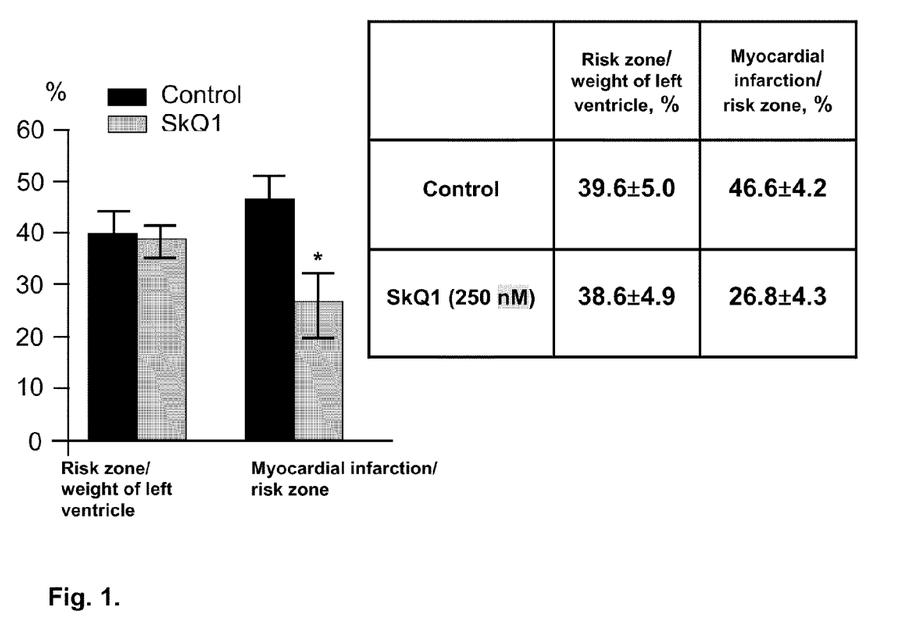
FIG. 1 shows the effect of preparation SkQ1 on myocardial infarction size caused by ischemia followed by reperfusion of Wistar rat hearts.

Histochemical analysis of the sections of the myocardium after reperfusion revealed no differences with regard to RZ/LV (%) between the groups. This indicated that damage to the coronary basin that supplies the left ventricle was identical in both groups. At the same time, in the group of animals received SkQ1, MI/RZ ratio was reliably 1.7 times less as compared to the control (P<0.005) (FIG. 1).

Thus, SkQ1 at a dose of 250 nmol/kg body weight/day exhibits cardioprotective properties—limits the size of experimental myocardial infarction in rats in situ reliably reducing ischemic and reperfusion injury of the heart.

2. The Effect of SkQ1 on $H_2O_2$-Induced Development of Arrhythmias in Isolated Rat Hearts Wistar rats received preparation SkQ1 daily for 3 weeks at doses of 2.0, 0.2 and 0.02 nmol/kg body weight by its addition to the curd. In the control group of animals, the feed was supplemented with sodium bromate in a similar dose. Experiments on isolated hearts were performed 1-2 days after the end of administration of the preparations by a standard technique under conditions of retrograde perfusion of the heart with a controlled rate of perfusion and a measurement of spontaneous heart rate. The effect of SkQ1 on the incidence of arrhythmias induced by injection of hydrogen peroxide (100 μM) into the coronary bed of hearts was studied. This model reproduces some features of a situation of oxidative stress that develops during reperfusion of ischemic heart.

Figure 2:
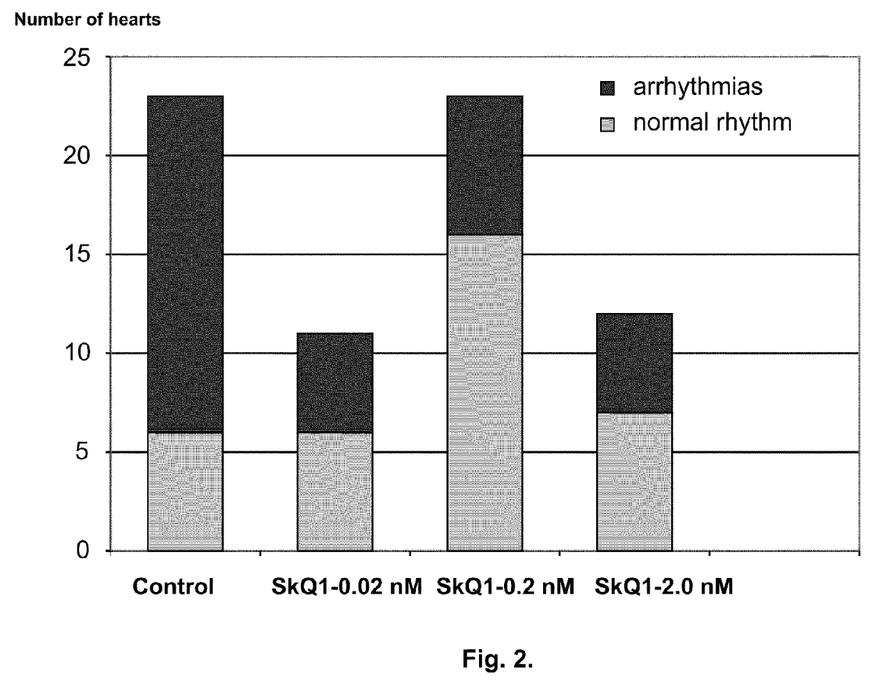
FIG. 2 shows the effect of SkQ1 on $H_2O_2$-induced development of arrhythmias in isolated hearts of Wistar rats.

Injection of hydrogen peroxide into the coronary bed of hearts of the control series by the $25^{th}$-$40^{th}$ minute was accompanied with the development of bradycardia and arrhythmia in most experiments, so that a sustainable heart rate persisted in only 26% of the experiments (FIG. 2). Automatism in hearts of rats received SkQ1 at doses of 0.02, 0.2 and 2.0 nmol/kg was more resistant to $H_2O_2$—the normal rhythm was maintained in 55, 70 and 58% of the experiments, respectively. The number of experiments in the control group and in the group received SkQ1 at a dose of 0.2 nmol/kg was the same—23, and the normal rhythm was documented in 6 control hearts and in 16 hearts from the group received SkQ1.

Thus, SkQ1 in the model system reduces the development of arrhythmias which develop during oxidative stress.

3. The Influence of SkQR1 on the Survival of Rats after Ischemia in a Single Kidney The survival of rats in which one kidney was removed and the second kidney was subjected to ischemia was studied. With ischemia in a single kidney, crisis occurs quite rapidly (2 days after ischemia), largely resulting in animal death. At the same time, with ischemia in one kidney, another kidney remains intact, and nothing fatal to the organism happens (apparently the intact kidney starts to perform double work).

In experiments on survival, rats were intraperitoneally injected with SkQR1 (SkQ1 derivative) in saline at a dosage of 1 μM 1 day before surgery, the final injection volume was 5 ml.

One day after the injection of the compound, the rats were laparotomized, the kidney and its vascular pedicle (renal artery and vein) were isolated, the kidney was separated from surrounding tissues to avoid lateral blood flow. Ischemia was performed on the left kidney, the right kidney remained intact or was removed. Ischemia was created by clamping the renal vascular pedicle with a clamp. Lack of blood flow in the kidney was monitored visually judging from a change in color of kidney tissue. Duration of ischemia varied from 60 to 90 minutes. After a period of ischemia, the clamps were removed and blood flowing into the kidney starts again, that moment was taken as the onset of reperfusion. An animal was put stitches, antiseptic on its wound and the anesthesia was stopped. The urine and blood samples were taken from the rats.

Figure 3:
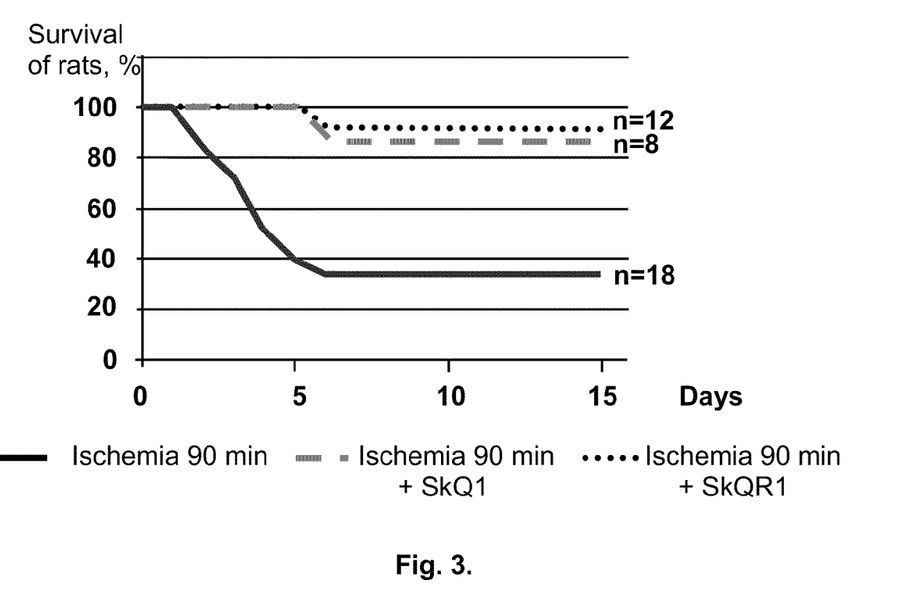
FIG. 3 shows the influence of SkQR1 on the survival of rats after ischemia in a single kidney.
Figure 5:
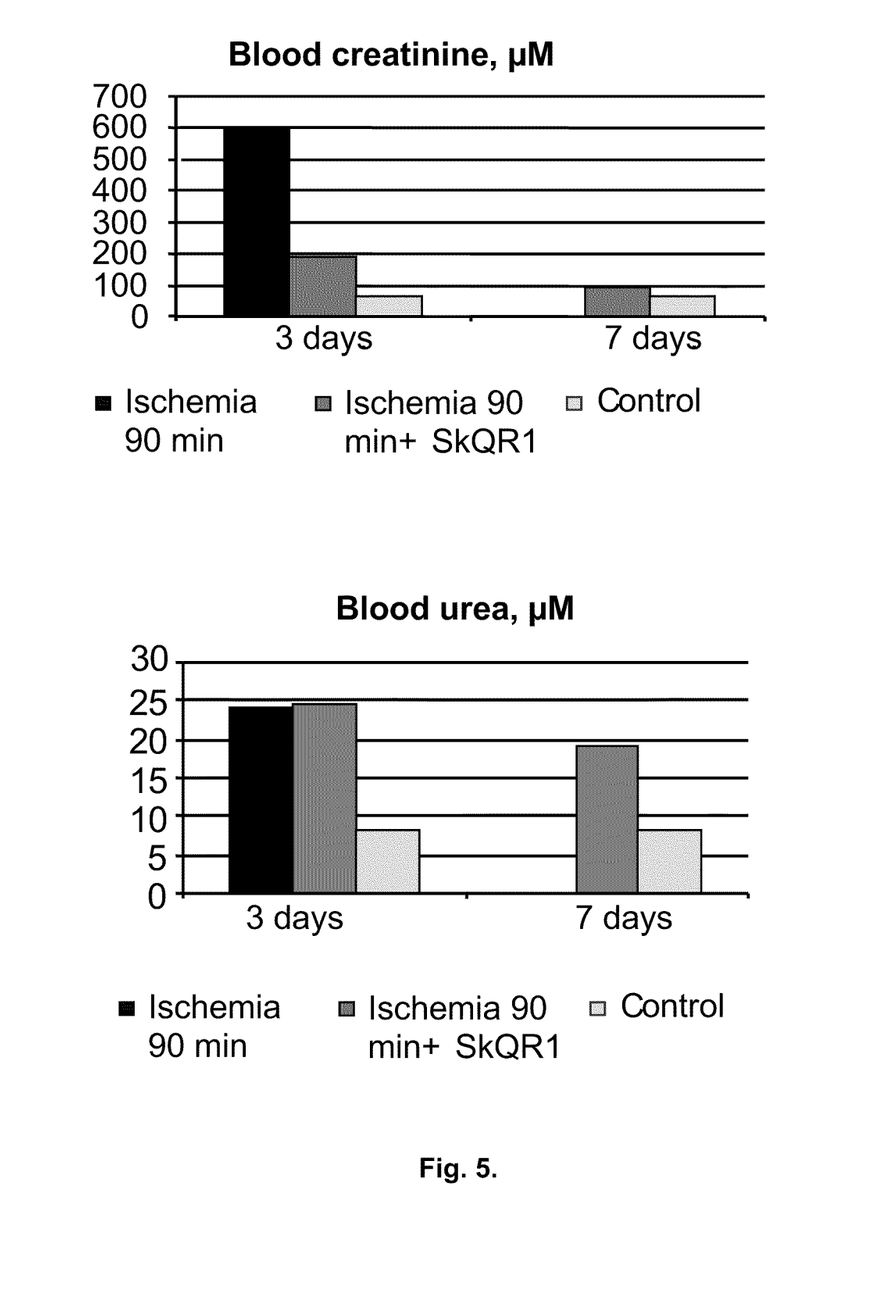
FIG. 5 shows the effect of SkQR1 on biochemical parameters of blood in rats with a single kidney after 90 minutes of ischemia.
Figure 6:
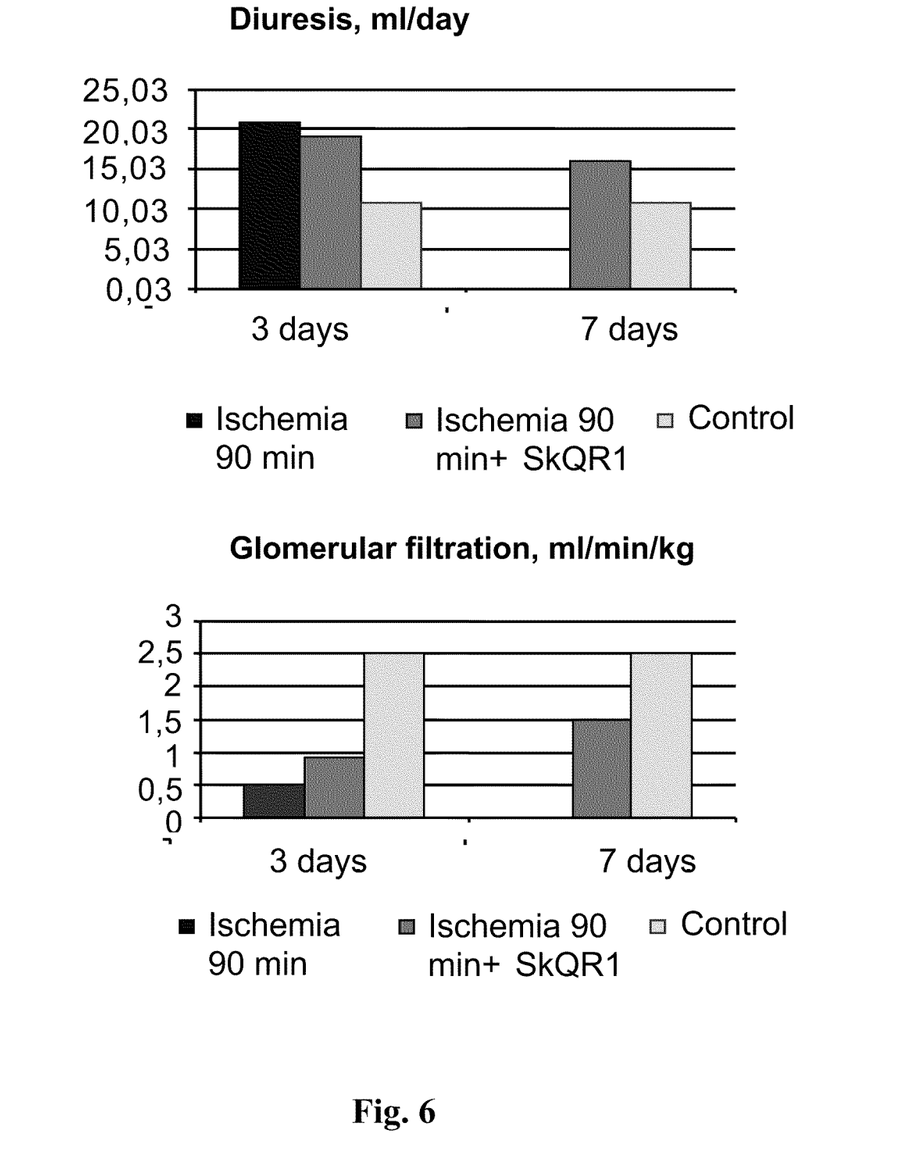
FIG. 6 shows the effect of SkQR1 on functional parameters (the amount of urine release, glomerular filtration rate) of a single kidney after 90 minutes of ischemia.

The distinct protective effect of SkQR1 on survival of rats in which a single kidney was subjected to ischemia/reperfusion was shown (FIG. 3). Normalization of a number of blood biochemical parameters (the creatinine and urea contents (FIG. 5)) and improvement in kidney function (glomerular filtration rate, the amount of urine release (FIG. 6)) in ischemic rats received SkQR1 were also observed.

4. The Antioxidant Activity of SkQR1 in Intact and Ischemic Kidney

Wistar rats divided into four groups were used in the experiment:

Group 1—intact rats were injected with preparation SkQR1 at a dose of 1 μmol/kg and after 1 day the production of reactive oxygen species was monitored judging from the intensity of the fluorescent probe 2',7'-dichlorofluorescein (DCF) in sections of the intact kidney.

Group 2—Study of production of reactive oxygen species in sections of the intact kidney without injection of Rh-SkQR1.

Group 3—prior intraperitoneal injection of Rh-SkQ in rats at a dose of 1 μmol/kg 1 day before the 40-minute ischemia of the kidney.

Group 4—40-minute ischemia of the kidney without injection of the preparation (control 2).

Wistar rats from groups 1 and 3 were intraperitoneally injected with 1 μmole/kg SkQR1 per day. Rats from groups 3 and 4 were subjected to heat ischemia of the left kidney by clamping the renal vessels for 40 minutes. Then, in the ischemic kidney, blood flow was restored for 10 minutes, after that the kidney was removed, the cortex was used to prepare thin sections with a thickness of 150-200 microns, the sections were incubated at 25° C. for 10 minutes in the incubation medium containing 10 mM 2',7'-dichlorofluorescein diacetate ether which is a fluorescent probe detecting reactive oxygen species, and fluorescence in renal tubules was investigated with the use of confocal laser microscope LSM 510 (Carl Zeiss, Germany). Fluorescence was excited by an argon laser at 488 nm with the fluorescence emission at 505-530 nm. For quantitative analysis of fluorescence intensity of dyes, confocal images of the kidney sections at zoom of ×10 and standardized microscope settings (laser excitation intensity, the extent of program signal amplification etc.) were obtained. The fluorescence intensity was evaluated using a 255-point scale, the area of zones with high fluorescence intensities (above 50 units) and the specific ratio of these areas to total fluorescence area were estimated.

Figure 4:
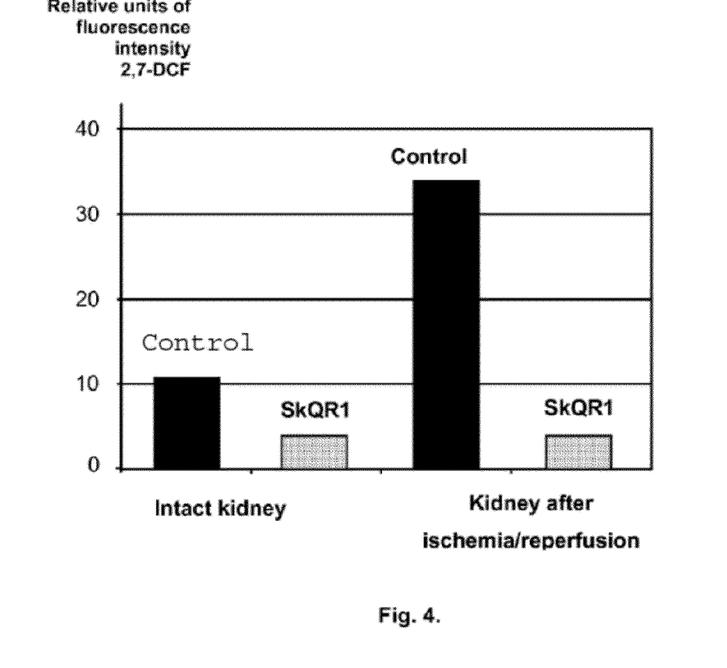
FIG. 4 shows the antioxidant activity of SkQR1 in intact and ischemic kidney.

The results showed (FIG. 4) that in intact rats, the fluorescence intensity of DCF in the kidney sections after injection of SkQR1 at a dose of 1 μmol/kg decreased from 11 to 4 relative units of fluorescence intensity as compared to the kidneys of rats which did not receive the preparation that indicates a high antioxidant activity of Rh-SkQ.

After 40 minutes of ischemia and 10 minutes of reperfusion, the formation of reactive oxygen species by mitochondria of renal tubules increased almost 3 times. At the same time, in the experiments with prior injection of SkQR1, the formation of reactive oxygen species in the kidney after 40 minutes of ischemia and 10 minutes of reperfusion remained at a low level comparable with normal values.

These results suggest that SkQR1 effectively suppresses the excess generation of reactive oxygen species in renal tubule epithelial cells, thereby providing the kidney with the effective protection against ischemic injury.

5. The Effect of SkQR1 on Behavioral Disorders Caused by Brain Hemorrhagic Stroke in Rats Neurobiological studies were performed on Wistar rats weighing from 150 to 220 g with the use of a model of brain hemorrhagic stroke induced by artificial compression ischemia. This model reproduces some features of a situation that develops during hemorrhagic stroke when blood flow presses on the brain leading to ischemia and subsequent atrophy of an area of the brain.

One day before surgery, rats were intraperitoneally injected with SkQR1 in saline at a dosage of 1 μmole, the final injection volume was 5 ml. Before surgery, rats were intraperitoneally injected with 3% solution of chloral hydrate at a dose of 350 mg/kg. The head of the anesthetized animal was fixed in the stereotactic device.

After fixation, the hair was shaved off from the head skin and a median longitudinal incision was made. At the place to be trepanned (over the parietal or frontal lobes of the cerebral cortex), the periosteum was separated. Using a cylindrical cutter with a diameter of 5 mm, trepanations were made in the parietal region of the animal skull departing 1 mm from the median suture. In order to avoid a thermocoagulation effect, the surface of the skull was cooled with saline during drilling. Dura mater was excised without damaging the brain surface.

To induce compression ischemia, Teflon rod was used which was inserted through the guiding glass tube into trepanations. Rod pressure on the brain surface was 40 mm Hg. Art. Compression of the cortex lasted for 15 minutes, then the rod was removed, the wound was treated with dry potassium salt of penicillin, the skin was sewn up and the suture was treated with 2% iodine solution.

During 6 days after ischemia, the behavior of the experimental animals (4 animals had ischemia only and 5 animals had ischemia and SkQR1 treatment) was studied using the test "open field".

Figure 7:
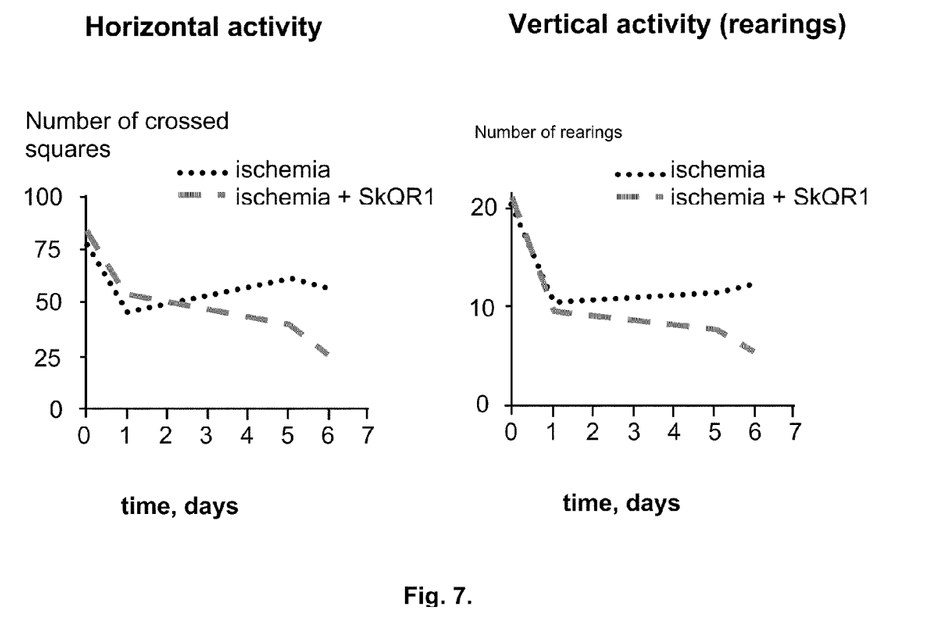
FIG. 7 shows the effect of the preparation on behavioral disorders caused by cerebral compression ischemia in Wistar rats (test "open field").

The first test was performed before administration of SkQR1 to animals, the second test was performed 24 hours after administration, just before ischemia. Based on the first test, the rats were divided into two groups approximately equal with respect to behavior and weight. The second test showed that intraperitoneal injection of SkQR1 had no noticeable effect on behavior of rats for one day (FIG. 7). The third and fourth tests showed a noticeable difference in behavior between treated and untreated animals. Increased horizontal and vertical activity of the untreated animals, as compared to the treated animals, indicates an increase in their emotional tension, anxiety (FIG. 7).

According to the literature, if rats pass the test "open field" for a few days, results with each subsequent test should be lower as compared to the previous one due to habituation of rats to a new environment. Rats administered SkQR1 revealed virtually the same behavior (FIG. 7) whereas a clear violation of that rule was found in the control individuals, also pointing to increased anxiety in untreated ischemic rats and indirectly to dysfunction in elements of their memory.

Thus, SkQR1 reduces the development of behavioral abnormalities caused by cerebral compression ischemia.

6. The Effect of SkQR1 on the Degree of Development of Brain Hemorrhagic Stroke in Rats On the seventh day of said experiment, neuromorphological analysis of the brain in the experimental animals was conducted using a model of brain hemorrhagic stroke. For neurohistological analysis, the experimental animals anesthetized with chloral hydrate were subjected to transcardiac perfusion using a modified Tellenitskii fixative, i.e., a mixture of formalin, alcohol, and acetic acid at a ratio of 2:7:1 (FAAC). Then the brain was extracted and paraffinated by a standard histological method and cut into sections with a thickness of 20 microns with a microtome. The paraffin sections were stained by the Nissl method. The sections were scanned and analyzed using the ImagJ program. The true value for the lesion volume was estimated using the Excel program.

Figure 8:
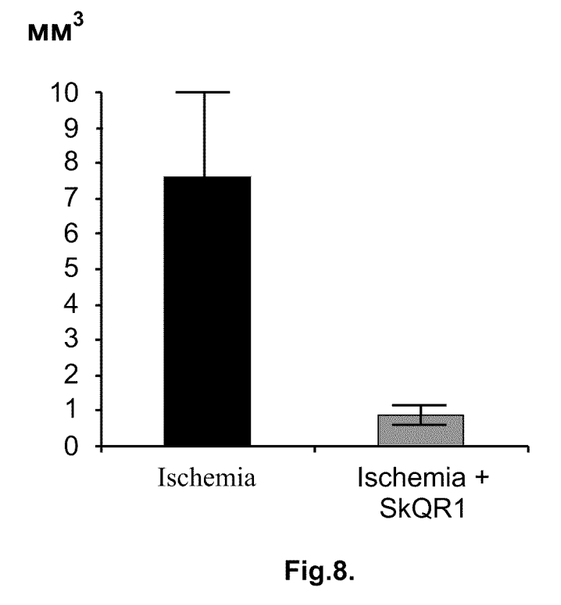
FIG. 8 shows the effect of the preparation on the lesion volume during cerebral compression ischemia in Wistar rats.

Under control conditions without pre-treatment with SkQR1, a significant brain damaged area adjacent to part of the brain directly affected by compression was observed. The lesion extends deep into the brain and the lesion volume can serve as an estimate of the degree of damage. The data of external examination of the rat brain demonstrate a clear trend to reduce the size and intensity of hemorrhagic focal lesions in the animals received SkQR1 prior to ischemia. Data for statistical analysis showed that the average size of the ischemic focus in animals which did not receive SkQR1 was 7.6 mm$^3$, whereas in animals received SkQR1—0.9 mm$^3$. (FIG. 8).

The results of said experiments suggest that SkQR1 is able to reduce the focus of brain hemorrhagic stroke.

The invention claimed is:
1. A pharmaceutical formulation comprising a compound which is SkQR1:

and its reduced form SkQR1H2:

wherein Z⁻ is a pharmacologically acceptable anion.

2. A method for decreasing the likelihood of developing damage to heart, brain, and/or kidney caused by ischemia and/or stroke, comprising administering to a subject in need thereof an effective amount of a pharmaceutical composition comprising a compound of Formula I:

wherein:
A is the effector moiety—antioxidant:

and/or reduced form thereof, wherein:
m is an integer from 1 to 3; and
each Y is methyl;
L is a linker group, comprising:
a) a straight or branched hydrocarbon chain which can be optionally substituted by one or more substituents and optionally contains one or more double or triple bonds; or
b) a natural isoprene chain;
n is an integer from 1 to 20; and
B is a targeting group, comprising Sk⁺Z⁻, wherein:
Sk⁺ is a lipophilic cation; and
Z⁻ is a pharmacologically acceptable anion; and
a pharmaceutically acceptable carrier thereof.

3. The method of claim 2, wherein the composition administered is a plastoquinone of structure:

wherein m=2.

4. The method of claim 2, wherein the compound of Formula I is SkQ1:

where Z⁻ is a pharmacologically acceptable anion.

5. The method of claim 2, wherein the compound of Formula I is SkQR1:

where Z⁻ is a pharmacologically acceptable anion.

* * * * *

UNITED STATES PATENT AND TRADEMARK OFFICE
CERTIFICATE OF CORRECTION

PATENT NO. : 8,518,915 B2
APPLICATION NO. : 12/667061
DATED : August 27, 2013
INVENTOR(S) : Skulachev et al.

It is certified that error appears in the above-identified patent and that said Letters Patent is hereby corrected as shown below:

In the Claims

Claim 1, Column 14 - lines 45-65 should read:

A pharmaceutical formulation comprising a compound which is SkQR1:

and its reduced form SkQR1H2:

wherein $Z^-$ is a pharmacologically acceptable anion.

Signed and Sealed this
Twenty-fourth Day of June, 2014

Michelle K. Lee
*Deputy Director of the United States Patent and Trademark Office*